(12) United States Patent
Madden et al.

(10) Patent No.: US 8,958,867 B2
(45) Date of Patent: Feb. 17, 2015

(54) DETECTION OF LIPID CORE PLAQUE CAP THICKNESS

(75) Inventors: Sean P. Madden, Arlington, MA (US); Joel S. Raichlen, Bryn Mawr, PA (US)

(73) Assignee: InfraReDx, Inc., Burlington, MA (US)

( * ) Notice: Subject to any disclaimer, the term of this patent is extended or adjusted under 35 U.S.C. 154(b) by 9 days.

(21) Appl. No.: 13/220,347

(22) Filed: Aug. 29, 2011

(65) Prior Publication Data

US 2013/0053698 A1    Feb. 28, 2013

(51) Int. Cl.
| | | |
|---|---|---|
| *A61B 6/00* | (2006.01) |
| *A61B 5/00* | (2006.01) |
| *A61B 5/02* | (2006.01) |
| *A61B 5/1459* | (2006.01) |
| *G01N 21/359* | (2014.01) |

(52) U.S. Cl.
CPC ........... *A61B 5/0075* (2013.01); *A61B 5/02007* (2013.01); *A61B 5/1459* (2013.01); *G01N 21/359* (2013.01)
USPC .......................................... 600/473; 600/476

(58) Field of Classification Search
USPC .................................. 600/473, 476; 382/128
See application file for complete search history.

(56) References Cited

U.S. PATENT DOCUMENTS

| | | | |
|---|---|---|---|
| 5,441,053 A | 8/1995 | Lodder et al. |
| 6,475,159 B1 | 11/2002 | Casscells et al. |
| 6,615,062 B2 | 9/2003 | Ryan et al. |
| 6,654,630 B2 | 11/2003 | Zuluaga et al. |
| 6,701,181 B2 | 3/2004 | Tang et al. |
| 6,706,004 B2 | 3/2004 | Tearney et al. |
| 6,816,743 B2 * | 11/2004 | Moreno et al. ................ 600/473 |
| 6,873,868 B2 | 3/2005 | Furnish |
| 6,895,137 B2 | 5/2005 | Zuluaga et al. |
| 6,904,199 B2 | 6/2005 | Zuluaga |
| 6,949,072 B2 | 9/2005 | Furnish et al. |
| 6,980,573 B2 | 12/2005 | Korn |
| 7,132,645 B2 | 11/2006 | Korn |
| 7,292,715 B2 | 11/2007 | Furnish |
| 7,310,357 B2 | 12/2007 | Zuluaga et al. |
| 7,313,432 B2 | 12/2007 | Tearney |
| 7,376,456 B2 | 5/2008 | Marshik-Geurts et al. |
| 7,426,410 B2 | 9/2008 | Zuluaga et al. |
| 7,450,241 B2 | 11/2008 | Zuluaga |
| 7,486,985 B2 | 2/2009 | Marshik-Geurts et al. |
| 7,535,935 B2 | 5/2009 | Korn |

(Continued)

OTHER PUBLICATIONS

510(K) Summary: LipiScan Coronary Imaging System, K072932, submitted by InfraReDx, Inc., available at http://www.accessdata.fda.gov/cdrh_docs/pdf7/K072932.pdf.

(Continued)

*Primary Examiner* — Baisakhi Roy
(74) *Attorney, Agent, or Firm* — Proskauer Rose LLP

(57) ABSTRACT

Described are methods, systems, and apparatus, including computer program products for examining a blood vessel wall. The blood vessel wall is illuminated with near-infrared light. Reflected near-infrared light from the blood vessel wall is received. A reflectance spectrum based on the reflected near-infrared light from the blood vessel wall is determined. Whether the reflectance spectrum is indicative of a presence of a lipid core plaque (LCP) by applying an LCP classifier to the reflectance spectrum is determined. A thickness of an LCP cap is determined by applying an LCP cap thickness classifier to the reflectance spectrum if the reflectance spectrum is indicative of the presence of the LCP. Indicia of the thickness of the LCP cap are displayed.

27 Claims, 7 Drawing Sheets

(56) References Cited

U.S. PATENT DOCUMENTS

| | | | |
|---|---|---|---|
| 7,539,530 B2 | 5/2009 | Caplan et al. | |
| 7,603,166 B2* | 10/2009 | Casscells et al. | 600/473 |
| 7,616,321 B2 | 11/2009 | Korn | |
| 7,672,713 B2 | 3/2010 | Furnish | |
| 7,679,754 B2 | 3/2010 | Zuluaga | |
| 7,689,268 B2 | 3/2010 | Marshik-Geurts et al. | |
| 7,742,805 B2 | 6/2010 | Furnish et al. | |
| 7,873,406 B2 | 1/2011 | Furnish et al. | |
| 7,929,145 B2 | 4/2011 | Zuluaga | |
| 8,000,774 B2* | 8/2011 | Sum et al. | 600/473 |
| 2002/0045811 A1* | 4/2002 | Kittrell et al. | 600/407 |
| 2004/0266734 A1* | 12/2004 | Danenberg et al. | 514/89 |
| 2005/0254061 A1* | 11/2005 | Alphonse | 356/479 |
| 2007/0003116 A1* | 1/2007 | Yuan et al. | 382/128 |
| 2007/0167836 A1* | 7/2007 | Scepanovic et al. | 600/476 |
| 2008/0221455 A1* | 9/2008 | Marshik-Geurts et al. | 600/473 |
| 2008/0249751 A1* | 10/2008 | Gadkar et al. | 703/2 |
| 2010/0317974 A1* | 12/2010 | Alfano et al. | 600/476 |
| 2011/0306956 A1* | 12/2011 | Islam | 606/15 |
| 2012/0129818 A1* | 5/2012 | Rajagopal | 514/158 |
| 2012/0302892 A1* | 11/2012 | Lue et al. | 600/476 |

OTHER PUBLICATIONS

510(K) Summary: InfraReDx LipiScan™ IVUS Imaging System, K093993, submitted by InfraReDx, Inc., available at http://www.accessdata.fda.gov/cdrh_docs/pdf9/K093993.pdf.

R. Virmani et al., "Pathology of the Vulnerable Plaque", J. Am. Coll. Cardiol. 2006; 47:C13-18.

E. Falk et al., "Coronary Plaque Disruption", Circulation 1995; 92:657-671, available at http://circ.ahajournals.org/content/92/3/657.short.

A. Finn et al., "Concept of Vulnerable/Unstable Plaque", Journal of the American Heart Association, Arteriosclerosis, Thrombosis, and Vascular Biology 2010; 30:1282-1292, available at http://atvb.ahajournals.org/content/30/7/1282.

G. Stone et al., "A Prospective Natural-History Study of Coronary Atherosclerosis", The New England Journal of Medicine 2011; 364:226-235.

H. Garcia-Garcia et al., "Tissue characterisation using intravascular radiofrequency data analysis: recommendations for acquisition, analysis, interpretation and reporting", EuroIntervention 2009; 5:177-189.

S. Takarada et al., "Effect of statin therapy on coronary fibrous-cap thickness in patients with acute coronary syndrome: Assessment by optical coherence tomography study", Atherosclerosis 2009; 202:491-497, available at www.elsevier.com/locate/atherosclerosis.

S. Chia et al., "Association of statin therapy with reduced coronary plaque rupture: an optical coherence tomography study", NIH Public Access Coron. Artery. Dis. Author Manuscript, published in final edited form as: Coron. Artery Dis. Jun. 2008; 19(4): 237-242.

G. van Soest et al., "Pitfalls in Plaque Characterization by OCT: Image Artifacts in Native Coronary Arteries", J. Am. Coll. Cardiol. Img. 2011;4;810-813, available at http://imaging.onlinejacc.org/cgi/content/full/4/7/810.

W. Jaross et al., "Determination of cholesterol in atherosclerotic plaques using near infrared diffuse reflection spectroscopy", Atherosclerosis 1999; 147:327-337.

V. Neumeister et al., "Determination of the cholesterol-collagen ratio of arterial atherosclerotic plaques using near infrared spectroscopy as a possible measure of plaque stability", Atherosclerosis 2002; 165:251-257.

C. Gardner et al., "Detection of Lipid Core Coronary Plaques in Autopsy Specimens With a Novel Catheter-Based Near-Infrared Spectroscopy System", J. Am. Coll. Cardiol. Img. 2008; 1:638-648, available at http://imaging.onlinejacc.org/cgi/content/full/1/5/638.

L. Rokach, "Taxonomy for characterizing ensemble methods in classification tasks: A review and annotated bibliography", Computational Statistics & Data Analysis 2009; 53:4046-4072.

P. Moreno et al., "Detection of Lipid Pool, Thin Fibrous Cap, and Inflammatory Cells in Human Aortic Atherosclerotic Plaques by Near-Infrared Spectroscopy", Circulation 2002; 105:923-927, available at http://circ.ahajournals.org/content/105/8/923.

P. Moreno et al., "Detection of High-Risk Atherosclerotic Coronary Plaques by Intravascular Spectroscopy", J. Interven. Cardiol. 2003; 16:243-252.

J. Wang et al., "Near-Infrared Spectroscopic Characterization of Human Advanced Atherosclerotic Plaques", J. Am. Coll. Cardiol. 2002; 39: 1305-1313.

A. Nilsson et al., "Near infrared diffuse reflection and laser-induced fluorescence spectroscopy for myocardial tissue characterisation", Spectrochimica Acta Part A: Molecular and Biomolecular Spectroscopy 1997; 53: 1901-1912.

L. Cassis et al., "Near-IR Imaging of Atheromas in Living Arterial Tissue", Anal. Chem. 1993; 65: 1247-1256.

E. Falk "Multiple culprits in acute coronary syndromes: systemic disease calling for systemic treatment", First published in Ital Heart J, vol. 1 Dec. 2000. (7 pages).

* cited by examiner

DETECTION OF LIPID CORE PLAQUE CAP THICKNESS

FIELD OF THE TECHNOLOGY

The present technology relates generally to the field of lipid core plaque cap thickness detection and, more specifically, to detection of lipid core plaque cap thickness using near-infrared spectroscopy.

BACKGROUND

The presence and characteristics of a lipid core are important considerations for assessing the risk of a coronary artery plaque. For a lipid core plaque ("LCP"), the thickness of the fibrous cap overlying the lipid-filled core is widely regarded as an important indication of the LCP's risk of rupture. LCPs displaying characteristics such as expansive remodeling, increased plaque volume, inflammation, lipid core, and cap thicknesses below, for example, approximately 0.065-0.1 mm can be classified as thin-capped fibroatheromas ("TFCAs"). TCFAs are the histopathologically-defined structures thought to be associated with in vivo vulnerable plaques and are the structures most often implicated, post-mortem, as the culprit site in sudden coronary deaths. As a result, the detection of LCP cap thickness in vivo is of great interest to the interventional cardiology community as a tool to assess future risk of LCP rupture.

Few existing techniques have sufficient capability to measure cap thickness, and the existing techniques capable of measuring cap thickness have deficiencies. For example, intravascular ultrasound ("IVUS") lacks adequate resolution to visualize the thickness of fibrous caps. IVUS is often utilized to estimate the presence of a thin cap overlying a plaque. Some approaches utilize definitions by which the apparent visual absence of a cap overlying a plaque is assumed to mean the cap thickness is below the typically-stated resolution limit of 40 MHz IVUS (100 µm). For example, in some IVUS approaches if echolucent plaque regions thought to be lipid cores seem to be in communication with the lumen, then the cap thickness is assumed to be below 100 µm, and if the plaque burden is also elevated, the structure is assumed to be an in vivo TCFA.

As another example, optical coherence tomography ("OCT") has adequate resolution (variously reported as tens of microns) to visualize the thickness of a fibrous cap. However, the accuracy of OCT techniques can be adversely affected by numerous image artifacts, and consensus recommendations for the inherently subjective offline interpretation of multiple cross sections per plaque have yet to be developed.

SUMMARY OF THE INVENTION

Accordingly, a need remains for techniques to rapidly, easily and accurately assess LCP cap thickness.

In one aspect, there is a computer-implemented method for examining a blood vessel wall. The method involves illuminating, with a probe, the blood vessel wall with near-infrared light. The method involves receiving, by the probe, reflected near-infrared light from the blood vessel wall. The method involves determining, by a computing device, a reflectance spectrum based on the reflected near-infrared light from the blood vessel wall. The method involves determining, by the computing device, whether the reflectance spectrum is indicative of a presence of a lipid core plaque by applying an LCP classifier to the reflectance spectrum. The method involves determining, by the computing device, a thickness of an LCP cap by applying an LCP cap thickness classifier to the reflectance spectrum if the reflectance spectrum is indicative of the presence of the LCP. The method involves displaying, on a display, indicia of the thickness of the LCP cap.

In another aspect, there is a computer program product, tangibly embodied in a non-transitory computer readable storage medium, for examining a blood vessel wall, the computer program product including instructions being operable to cause a data processing apparatus to receive a signal indicative of reflected near-infrared light from the blood vessel wall, the blood vessel wall having been illuminated with near-infrared light; determine a reflectance spectrum based on the received signal; determine whether the reflectance spectrum is indicative of a presence of a LCP by applying an LCP classifier to the reflectance spectrum; determine a thickness of an LCP cap by applying an LCP cap thickness classifier to the reflectance spectrum if the reflectance spectrum is indicative of the presence of the LCP; and display, on a display, indicia of the thickness of the LCP cap.

In another aspect, there is a computer-implemented method for building a LCP cap thickness classifier. The method includes performing the following for each location of a plurality of locations on a plurality of blood vessel walls: illuminating, with a probe, the location with near-infrared light; receiving, by the probe, reflected near-infrared light from the location; determining, by a computing device, a reflectance spectrum based on the reflected near-infrared light from the location; determining, by the computing device, whether the reflectance spectrum is indicative of a presence of an LCP at the location by applying an LCP classifier to the reflectance spectrum; selecting, by the computing device, the location if the reflectance spectrum is indicative of the presence of the LCP at the location; and receiving, by the computing device, histopathology data associated with the location. The method involves receiving, by the computing device, a cap thickness threshold. The method involves generating, by the computing device, the LCP cap thickness classifier based on the reflectance spectrum and histopathology data of each selected location and the cap thickness threshold.

In another aspect, there is a computer program product, tangibly embodied in a non-transitory computer readable storage medium, for building a LCP cap thickness classifier, the computer program product including instructions being operable to cause a data processing apparatus to, for each location of a plurality of locations on a plurality of blood vessel walls: receive a signal indicative of reflected near-infrared light from the location, the location having been illuminated with near-infrared light; determine a reflectance spectrum based on the received signal; determine whether the reflectance spectrum is indicative of a presence of an LCP at the location by applying an LCP classifier to the reflectance spectrum; select the location if the reflectance spectrum is indicative of the presence of the LCP at the location; and receive histopathology data associated with the location. The computer program product includes instructions being operable to cause a data processing apparatus to receive a cap thickness threshold and generate the LCP cap thickness classifier based on the reflectance spectrum and histopathology data of each selected location and the cap thickness threshold.

Any of the above aspects can include one or more of the following features. In some embodiments, the LCP cap thickness classifier comprises a mathematical model generated based on one or more sample reflectance spectra and associated histopathology data. In some applications, the histopathology data comprises LCP cap thickness measurements. In some embodiments, applying the LCP cap thickness classifier provides a probability that the thickness of the LCP cap exceeds a threshold thickness. In some embodiments, applying the LCP cap thickness classifier provides a probability that the thickness of the LCP cap is less than a threshold thickness. In some applications, the threshold thickness is approximately 0.4 millimeters. In some applications, the threshold thickness is approximately 0.1 millimeters.

In some embodiments, the method includes determining a thickness of the LCP cap by applying a second LCP cap thickness classifier to the reflectance spectrum if the reflectance spectrum is indicative of the presence of the LCP.

In some embodiments, the indicia of the thickness of the LCP cap comprises an indication that the thickness of the LCP cap exceeds a thickness threshold. In some embodiments, the indicia of the thickness of the LCP cap comprises an indication that the thickness of the LCP cap is less than a thickness threshold.

In some embodiments, the computer program product includes instructions being operable to cause the data processing apparatus to determine a thickness of the LCP cap by applying a second LCP cap thickness classifier to the reflectance spectrum if the reflectance spectrum is indicative of the presence of the LCP.

Other aspects and advantages of the present invention will become apparent from the following detailed description, taken in conjunction with the accompanying drawings, illustrating the principles of the invention by way of example only.

BRIEF DESCRIPTION OF THE DRAWINGS

The foregoing and other objects, features, and advantages of the present technology, as well as the technology itself, will be more fully understood from the following description of various embodiments, when read together with the accompanying drawings, in which.

DETAILED DESCRIPTION

The technology provides methods and apparatus utilizing near-infrared spectroscopy for the in vivo examination of blood vessel walls and the classification of the thickness of LCP caps. The technology leverages the near-infrared spectral differences between the various biochemical components of healthy blood vessel tissue versus a cholesterol-laden LCP to characterize LCP cap thickness.

In some embodiments, the technology can be used to identify plaque characteristics thought to be associated with an LCP's vulnerability to rupture. Such vulnerable LCPs can be generally described as LCPs that are prone, with or without a triggering activity or event of a patient, to events such as ulceration, rupture, or erosion leading to thrombosis causing an acute ischemic syndrome. For example, the technology can be used to non-destructively identify thin-capped atherosclerotic LCPs, which may be vulnerable and more likely to rupture. In some applications, the information about particular LCPs provided by the technology can facilitate physicians in determining the appropriate pharmaceutical or procedural interventions to address those LCPs. In some applications, the information about particular LCPs provided by the technology can facilitate evaluating a particular pharmaceutical's effectiveness for treating particular LCPs.

Figure 1:
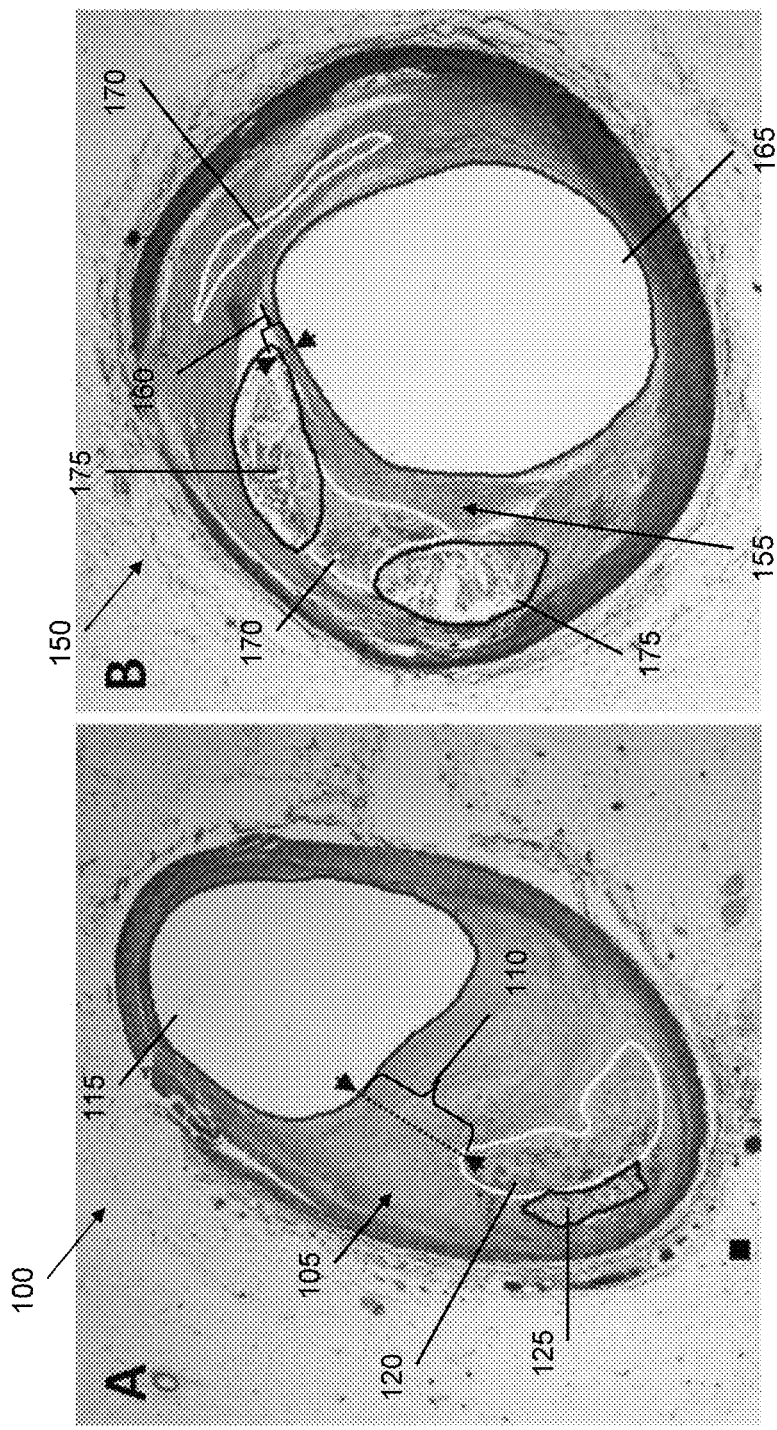
FIG. 1 depicts two sample artery cross sections, each containing LCPs.

FIG. 1 depicts two sample artery cross sections, each containing LCPs. Artery cross section 100 shows the lumen 115, fibrotic tissue 105, and lipid-rich structures consistent with an LCP: lipid pool. The fibrotic tissue 105 constitutes a very thick cap overlying the lipid-containing portions of the plaque, even at its thinnest region 110. In some instances, such as this example, a very thick cap can be a cap with a minimum thickness exceeding 0.4 mm. Artery cross section 150 is an example of an artery containing lipid-rich structures consistent with an LCP: lipid pools 170 and necrotic cores 175. The fibrotic tissue 155 separating the LCP structures from the lumen 165 has a very thin region 160. In some instances, a very thin cap can be a cap with a minimum thickness less than 0.1 mm. The plaque shown in cross section 150 can be considered vulnerable, as region 160 may be more likely to rupture and release the contents of lipid pools 170 and necrotic cores 175 into lumen 165, which can lead to arterial thrombosis and loss of blood flow to the heart tissue.

Figure 2A:
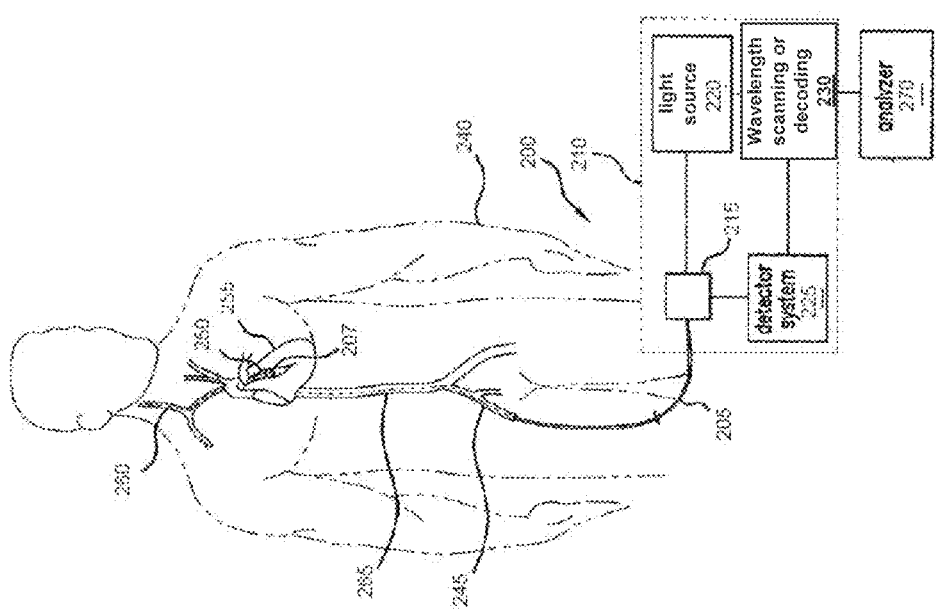
FIG. 2A depicts an optical spectroscopic catheter system.

Various instruments can be used as a part of or in conjunction with the technology to perform near-infrared spectroscopy. FIG. 2A depicts an optical spectroscopic catheter system 200. Catheter system 200 can generally be used for blood vessel analysis. For example, catheter system 200 can be used to illuminate a blood vessel wall with near-infrared light and receive reflected near-infrared light from the blood vessel wall. The technology can use the received reflected near-infrared light to assess the cap thickness of detected LCPs.

Catheter system 200 includes a probe or catheter 205, and a spectrometer system 210. Catheter 205 can include catheter head 207. Spectrometer system 210 includes pullback and rotation device 215, light source 220, detector system 225, and wavelength scanning or decoding device 230.

Catheter 205 can include an optical fiber or optical fiber bundle (not shown). Catheter 205 can be inserted into the patient 240 via a peripheral vessel, such as the femoral artery 245. The catheter head 207 can then be moved to a desired target area within a blood vessel, such as coronary artery 250 of heart 255 or carotid artery 260. In the illustrated example, this is achieved by moving catheter head 207 up through the aorta 265.

Once catheter head 207 is located at a site for examination within a blood vessel, radiation can be generated. In the illustrated example, near-infrared radiation is generated by light source 220 and tuned over a range of wavelengths covering one or more spectral bands of interest. In other embodiments, one or more broadband sources are used to provide the spectral bands of interest, and the signal intensity at various wavelengths is determined using a spectrometer or wavelength encoding methodology. In either case, the optical signals can be coupled into the optical fiber of catheter 205 to be transmitted to catheter head 207.

In some embodiments, near-infrared spectral bands are used for spectroscopy. Exemplary spectral bands include light having wavelength of 1000 to 1450 nanometers (nm), 1000 nm to 1350 nm, 1100 nm to 1900 nm, 1150 nm to 1250 nm, 1175 nm to 1280 nm, and 1190 nm to 1250 nm. Other exemplary spectral bands include 1660 nm to 1740 nm, and 1630 nm to 1800 nm. In some implementations, the spectral response is first acquired for a full spectral region and then bands are selected within the full spectral region for further analysis.

In some embodiments, the received, diffusely-reflected, near-infrared light is transmitted back down the optical fibers of catheter 205 to pullback and rotation device 215 or in separate optical fibers. This provides the received radiation or optical signals to a detector system 225, which can comprise one or multiple detectors.

Wavelength scanning or decoding device 230 monitors the response of catheter system 200, while controlling light source 220 in order to probe the spectral response of a target area (e.g., an inner wall of a blood vessel) and through the intervening blood or other unwanted signal source, which is typically a fluid.

As a result, spectrometer system 210 can collect spectra. When the acquisitions of the spectra are complete, the spectrometer system 210 then provides the data to the analyzer 270.

Figure 2B:
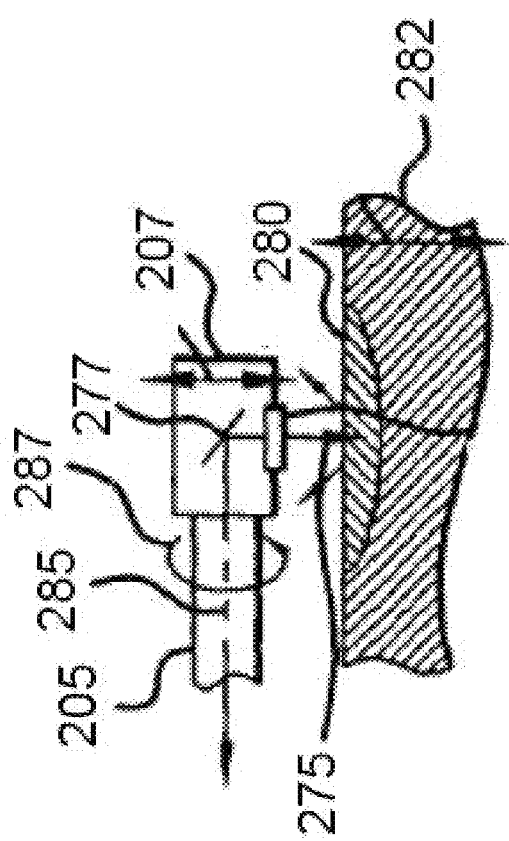
FIG. 2B depicts an alternate view of a portion of the catheter of FIG. 2A.

FIG. 2B depicts an alternate view of a portion of catheter 205 of FIG. 2A. The optical signal 275 (e.g., near-infrared radiation) from the optical fiber of the catheter 205 is directed by fold mirror 277, for example, to exit from the catheter head 207 and impinge on target area 280 of blood vessel wall 282. Catheter head 207 then collects the light that has been diffusely reflected from the target area 280 and the intervening fluid and returns reflected radiation 285 back down catheter 205.

In one embodiment, the catheter head 207 spins as illustrated by arrow 287. This allows the catheter head 207 to scan a complete circumference of the blood vessel wall 282. In other embodiments, catheter head 207 includes multiple emitter and detector windows, preferably being distributed around a circumference of the catheter head 207. In some examples, the catheter head 207 is spun while being drawn-back through the length of the portion of the vessel being analyzed.

The analyzer 270 can receive reflected radiation 285 and make an assessment of the blood vessel wall 282 or other tissue of interest (e.g., tissue at area 280 that is opposite catheter head 207). In some embodiments, analyzer 270 determines a reflectance spectrum based on reflected radiation 285. In some embodiments, the reflectance spectrum can be a diffuse reflectance spectrum or log-transformed reflectance spectrum. In some embodiments, an absorbance spectrum can be determined, where absorbance is provided by equation 1.

$$\text{Absorbance} = -\log(I/I_0) \quad \text{EQN. 1}$$

In equation 1, I is the detected intensity of reflected radiation and $I_0$ is the incident intensity. As will be described in detail below, analyzer 270 can assess the cap thickness of LCPs based on the determined spectrum.

Building an LCP Cap Thickness Classifier

Figure 3:
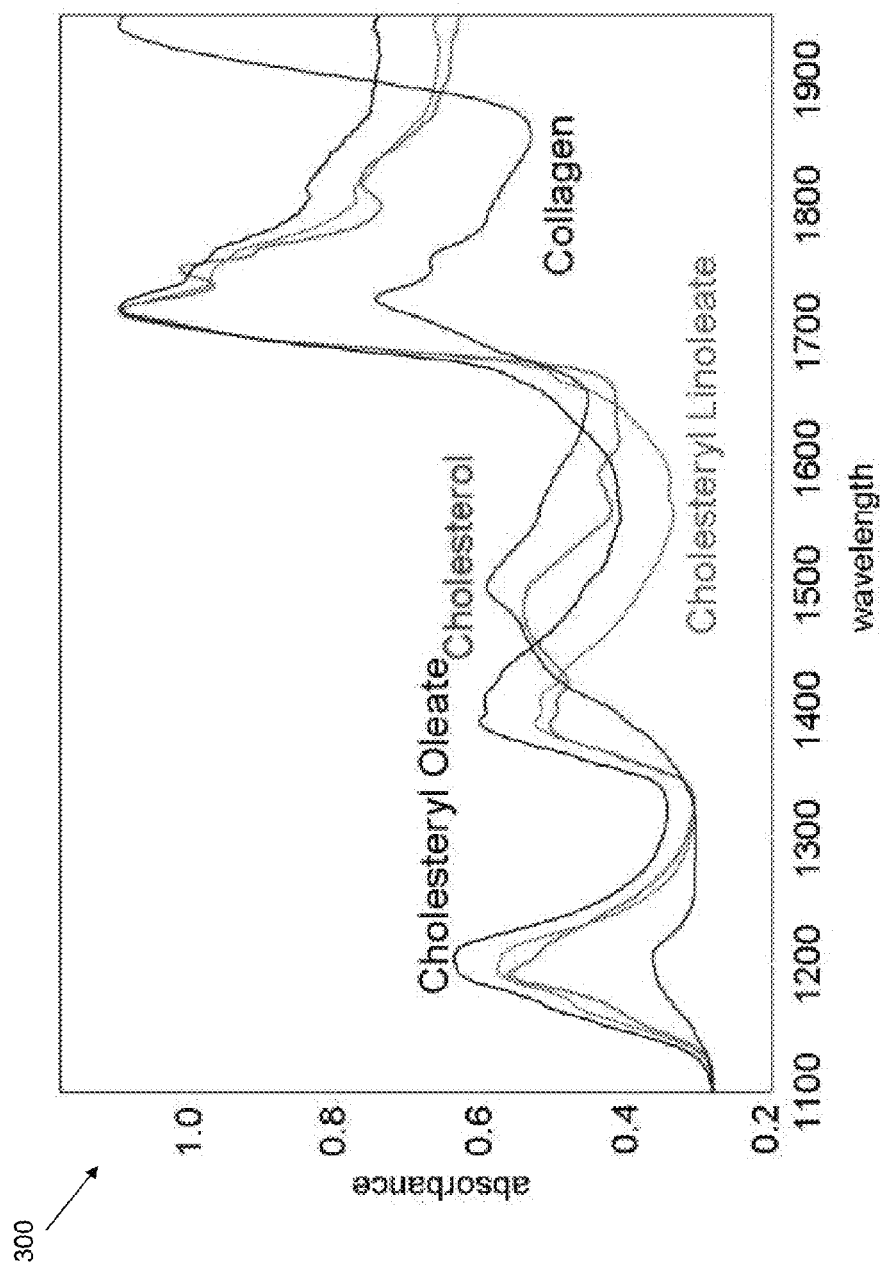
FIG. 3. is a graph of exemplary near-infrared absorbance spectra for different substances.

As noted above, the technology leverages the near-infrared spectral differences between various biochemical components of healthy blood vessel tissue versus a cholesterol-laden LCP. FIG. 3. is a graph 300 of exemplary near-infrared absorbance spectra for different substances. Graph 300 includes near-infrared spectra for various forms of cholesterol, including cholesteryl oleate, cholesterol, and cholesteryl linoleate, along with collagen. Healthy blood vessel tissue is rich in collagen, whereas LCPs will contain higher relative cholesterol content. Graph 300 illustrates the spectral differences between collagen and the various cholesterol forms, which the present technology uses to assess LCP cap thickness.

In some embodiments, the technology involves building a mathematical classifier or model to classify the thickness of LCP caps. The mathematical classifier can be developed by modeling the relationship between spectra and tissue states of known tissue samples (e.g., samples for which the LCP cap's thickness is known).

Figure 4:
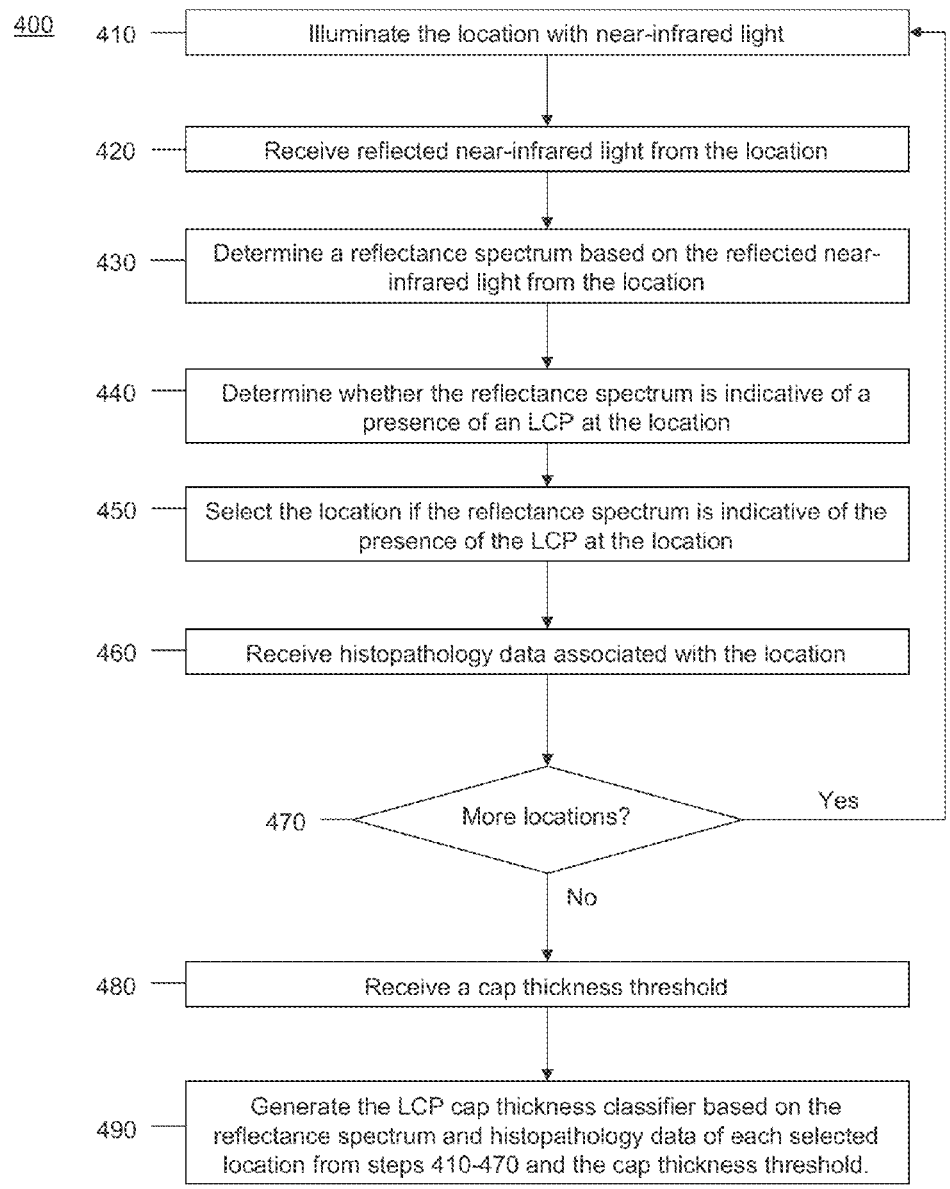
FIG. 4 is a flow chart that depicts a method of building a LCP cap thickness classifier.

FIG. 4 is a flow chart 400 that depicts a method of building a LCP cap thickness classifier. In some embodiments, spectroscopic catheter system 200 of FIG. 2A can perform the method of building a LCP cap thickness classifier. In some embodiments, a separate computing device can perform the method of building a LCP cap thickness classifier.

At step 410, a location in a blood vessel is illuminated with near-infrared light. As described above with reference to FIG. 2A, catheter system 200, for example, can be used to illuminate a location in a blood vessel with near-infrared light. The near-infrared light can include near-infrared light within a particular spectral band. Exemplary spectral bands include 1000 to 1450 nanometers (nm), 1000 nm to 1350 nm, 1100 nm to 1900 nm, 1150 nm to 1250 nm, 1175 nm to 1280 nm, and 1190 nm to 1250 nm. Other exemplary spectral bands include 1660 nm to 1740 nm, and 1630 nm to 1800 nm. At step 420, reflected near-infrared light from the location is received. For example, catheter system 200 can receive near-infrared light reflected from the location.

At step 430, a reflectance spectrum is determined based on the reflected near-infrared light from the location. In some embodiments, analyzer 270 can determine a reflectance spectrum based on the reflected near-infrared light from the location. In some embodiments, the reflectance spectrum can be a diffuse reflectance spectrum or log-transformed reflectance spectrum. In some embodiments, an absorbance spectrum can be determined.

At step 440, it is determined whether the reflectance spectrum is indicative of a presence of an LCP. In some embodiments, whether the reflectance spectrum is indicative of a presence of an LCP can be determined using the methods described in U.S. Pat. No. 8,000,774, titled "Method and System for Intra Luminal Thrombosis Detection," and filed Jan. 3, 2007 by Sum et al., the entire contents of which are hereby incorporated by reference. In some embodiments, whether the reflectance spectrum is indicative of a presence of an LCP can be determined using the methods described in U.S. Pat. No. 6,816,743, titled "Methods and Apparatus for in vivo Identification and Characterization of Vulnerable Atherosclerotic Plaques," and filed Jan. 24, 2001 by Moreno et al., the entire contents of which are hereby incorporated by reference. At step 450, the location is selected if the reflectance spectrum is indicative of the presence of the LCP at the location.

At step 460, histopathology data associated with the location is received. Histopathology data can include data obtained by visual inspection of the location. For example, a histopathologist can examine a cross section of the vessel at the location to determine whether an LCP is present and the thickness of the LCP's cap. These data can be provided in a database or other suitable storage device.

At step 470, it is determined whether there are more vessel wall locations from which to collect data. If there are more locations in the plurality of vessels left from which to receive spectra and histopathology data, steps 410-460 are repeated for each remaining location. Otherwise, the method proceeds to step 480.

At step 480, a cap thickness threshold is received (e.g., approximately 0.4 mm or 0.1 mm).

At step 490, the LCP cap thickness classifier is generated based on the reflectance spectrum and histopathology data of each selected location from steps 410-470 and the cap thickness threshold. In some embodiments, the data is set up as an "x-block" matrix, where each row represents a spectrum for a corresponding location, and a "y-block" vector of histopathology data (e.g., cap thickness reference values) for the corresponding location. In some embodiments, the cap thickness threshold is applied to the vector of histopathology data, resulting in a "y-block" that indicates the presence or absence of a cap with a thickness greater than the cap thickness threshold. In some embodiments, the cap thickness threshold is applied to the vector of histopathology data, resulting in a "y-block" that indicates the presence or absence of a cap with a thickness less than the cap thickness threshold.

The cap thickness classifier can then be generated using any of several multivariate techniques, such as multivariate mathematical models developed by modeling the relationship between the reflectance spectra and histopathology data for each location. The mathematical models can be based upon techniques such as Partial Least Squares Discrimination Analysis (PLS-DA), Principle Component Analysis with Mahalanobis Distance and augmented Residuals (PCA/MDR), and others such as PCA with K-nearest neighbor, PCA with Euclidean Distance, SIMCA, the bootstrap error-adjusted single-sample technique (BEST), neural networks and support vector machines, and other types of discrimination means.

In some embodiments, multiple classifiers can be generated. For example, a first classifier can be generated using a cap thickness threshold corresponding to a thick LCP cap (e.g., approximately 0.4 mm) and a second classifier can be generated using a cap thickness threshold corresponding to a thin LCP cap (e.g., approximately 0.1 mm).

Examining a Blood Vessel Wall

Figure 5:
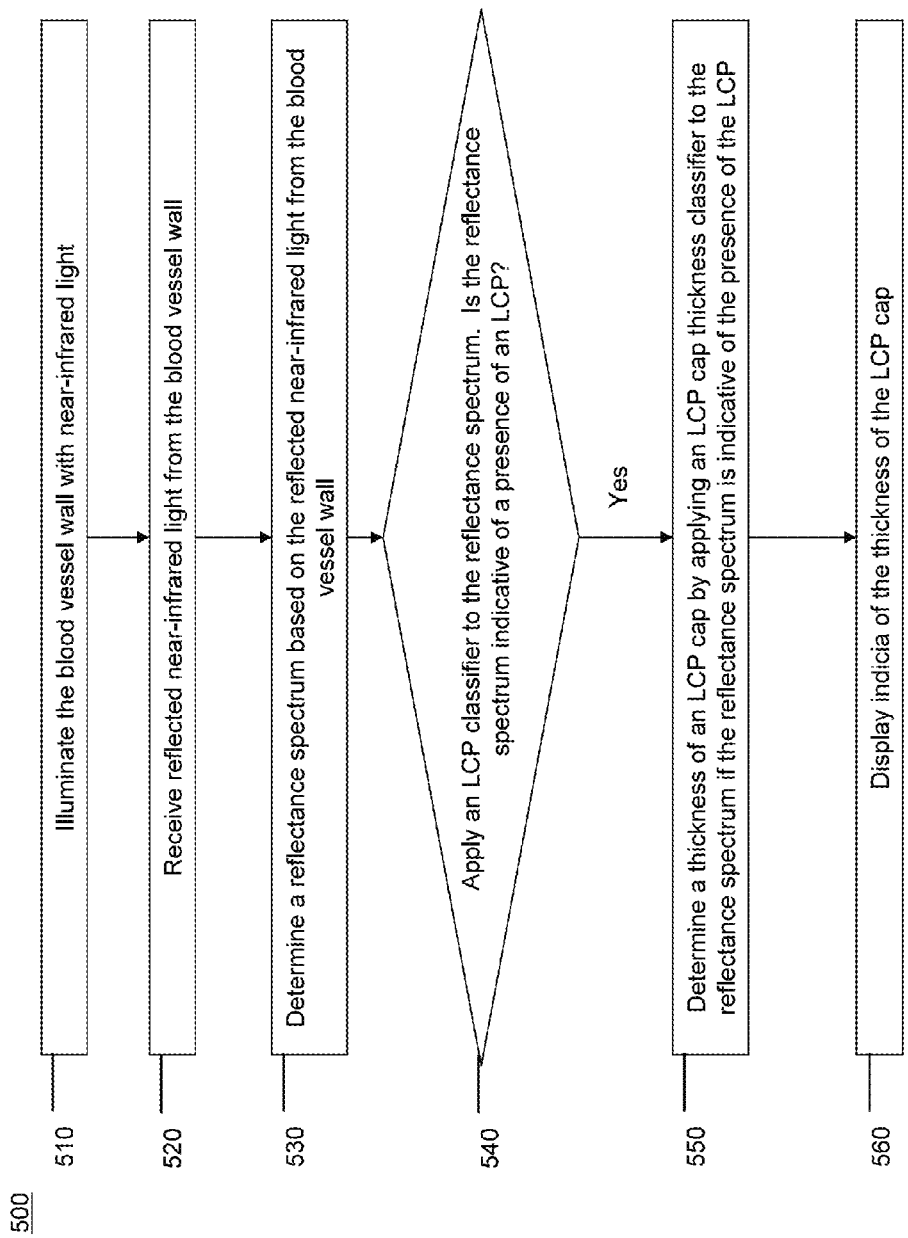
FIG. 5 is a flow chart that depicts a method for examining a blood vessel wall and generating the indicia of the thicknesses of the LCP caps.

In some embodiments, the technology involves a method of examining a blood vessel wall and generating the indicia of the thicknesses of the LCP caps. FIG. 5 is a flow chart 500 that depicts a method for examining a blood vessel wall. In some embodiments, spectroscopic catheter system 200 of FIG. 2A can perform the method of examining a blood vessel wall. In some embodiments, a separate computing device can perform the method of examining a blood vessel wall.

At step 510, the blood vessel wall is illuminated with near-infrared light. As described above with reference to FIG. 2A, catheter system 200, for example, can be used to illuminate a blood vessel with near-infrared light. The near-infrared light can include near-infrared light within a particular spectral band. Exemplary spectral bands include 1000 to 1450 nanometers (nm), 1000 nm to 1350 nm, 1100 nm to 1900 nm, 1150 nm to 1250 nm, 1175 nm to 1280 nm, and 1190 nm to 1250 nm. Other exemplary spectral bands include 1660 nm to 1740 nm, and 1630 nm to 1800 nm. At step 520, reflected near-infrared light from the blood vessel wall is received. For example, catheter system 200 can receive near-infrared light reflected from the location.

At step 530, a reflectance spectrum is determined based on the reflected near-infrared light from the blood vessel wall. In some embodiments, analyzer 270 can determine a reflectance spectrum based on the reflected near-infrared light from the blood vessel wall. In some embodiments, the reflectance spectrum can be a diffuse reflectance spectrum or log-transformed diffuse reflectance spectrum. In some embodiments, an absorbance spectrum can be determined.

At step 540, it is determined whether the reflectance spectrum is indicative of a presence of an LCP. Any of the techniques previously described with respect to step 450 of FIG. 4 can be used. If the reflectance spectrum is indicative of a presence of an LCP, the method proceeds to step 550.

At step 550, a thickness of an LCP cap is determined by applying an LCP cap thickness classifier to the reflectance spectrum if the reflectance spectrum is indicative of the presence of the LCP.

In some embodiments, the LCP cap thickness classifier can be a classifier generated as described above with reference to FIG. 4. The LCP cap thickness classifier is applied to the spectrum to characterize the tissue at a particular location along the vessel wall. For example, application of the LCP cap thickness classifier to the reflectance spectrum can provide a probability that the spectrum is indicative of an LCP cap with a cap thickness greater than the cap thickness threshold used to build the LCP cap thickness classifier. In such embodiments, the cap thickness is determined to be greater than the cap thickness threshold if the probability provided by classifier exceeds a threshold (e.g., 0.6). Application of the LCP cap thickness classifier to the reflectance spectrum can provide a probability that the spectrum is indicative of an LCP cap with a cap thickness less than the cap thickness threshold used to build the LCP cap thickness classifier. In such embodiments, the cap thickness is determined to be less than the cap thickness threshold if the probability provided by classifier exceeds a threshold (e.g., 0.6).

In some embodiments, multiple classifiers can be applied. For example, a first classifier can be applied with a cap thickness threshold corresponding to a thick LCP cap (e.g., approximately 0.4 mm) and a second classifier can be applied using a cap thickness threshold corresponding to a thin LCP cap (e.g., approximately 0.1 mm). In some embodiments, the results of multiple classifiers are combined into a single classifier.

Figure 6:
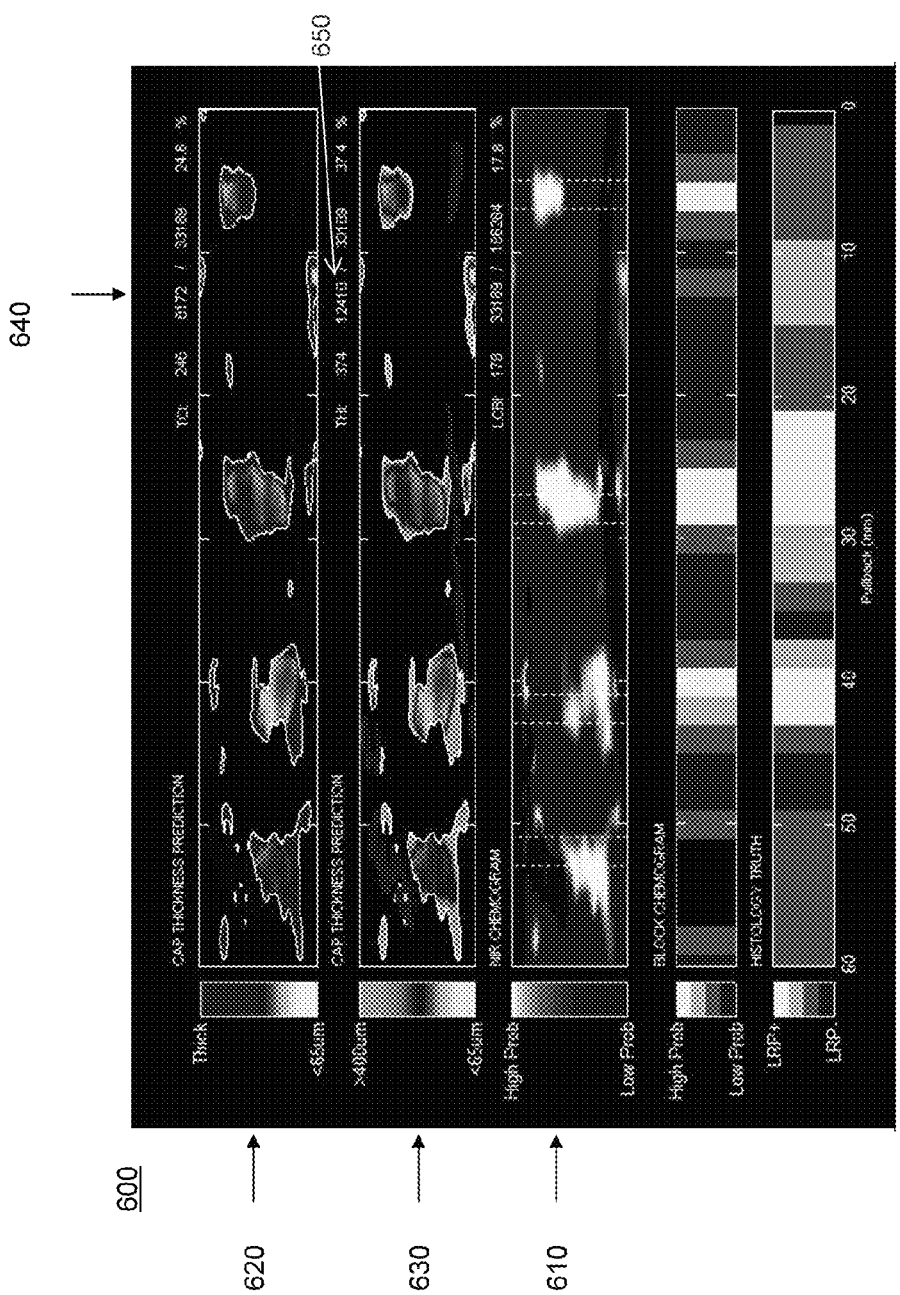
FIG. 6 depicts an exemplary graphical display 600 for displaying indicia of the thickness of LCP caps.

At step 560, indicia of the thickness of the LCP cap is displayed. In some embodiments, the indicia of the thickness of the LCP cap are displayed on a graphical display. FIG. 6 depicts an exemplary graphical display 600 for displaying indicia of the thickness of LCP caps. Plot 610 on graphical display 600 shows a spatially-resolved view of the presence of LCPs, as provided by an LCP classifier, for example. Plot 620 shows a spatially-resolved view of indicia of the thickness of LCP caps, as provided by an LCP cap thickness classifier. As described above, application of an LCP cap thickness classifier to the reflectance spectrum can provide a probability that the spectrum is indicative of an LCP cap with a cap thickness greater than the cap thickness threshold used to build the LCP cap thickness classifier. Plot 620 maps this probability to a two-shade scale, with heavily-shaded regions indicating locations in the vessel with an LCP cap that the classifier predicted to have a cap thickness greater than the threshold cap thickness with a probability that exceeds a threshold (e.g., 0.6) and the lightly-shaded regions indicating locations in the vessel with an LCP cap that the classifier predicted to have a cap thickness greater than the threshold cap thickness with a probability that is less than a threshold (e.g., 0.6). Plot 630 shows a spatially-resolved view of indicia of the thickness of LCP caps, as provided by a LCP cap thickness classifier. Plot 620 maps the same probabilities to a three-shade scale, in order to accentuate which areas were predicted to have very thick caps (intermediate shading) (e.g., a probability of greater than 0.6), which areas were predicted to have very thin caps (light shading) (e.g., a probability of less than 0.4), and which areas the classifier provided an intermediate probability (heavy shading) (e.g., a probability between 0.4 and 0.6).

Graphical display 600 also includes thin 640 and thick cap index summary numbers 650, showing the number and percent of evaluated LCP pixel locations predicting below a cap thickness threshold for thin caps or above a cap thickness threshold for thick caps.

The above-described techniques can be implemented in digital electronic circuitry, or in computer hardware, firmware, software, or in combinations of them. The implementation can be as a computer program product, i.e., a computer program tangibly embodied in an information carrier, e.g., in a machine-readable storage device, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps can be performed by one or more programmable processors executing a computer program to perform functions of the invention by operating on input data and generating output. Method steps can also be performed by, and apparatus can be implemented as, special purpose logic circuitry, e.g., an FPGA (field programmable gate array) or an ASIC (application-specific integrated circuit). Modules can refer to portions of the computer program and/or the processor/special circuitry that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. Generally, a computer also includes, or can be operatively coupled to receive data from or transfer data to, or both, one or more mass storage devices for storing data, e.g., magnetic, magneto-optical disks, or optical disks. Data transmission and instructions can also occur over a communications network. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

To provide for interaction with a user, the above described techniques can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The above described techniques can be implemented in a distributed computing system that includes a back-end component, e.g., as a data server, and/or a middleware component, e.g., an application server, and/or a front-end component, e.g., a client computer having a graphical user interface and/or a Web browser through which a user can interact with an example implementation, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the Internet, and include both wired and wireless networks.

The computing system can include clients and servers. A client and server are generally remote from each other and typically interact through a communication network. The relationship of client and server arises by virtue of computer programs running on the respective computers and having a client-server relationship to each other.

The technology has been described in terms of particular embodiments. The alternatives described herein are examples for illustration only and not to limit the alternatives in any way. The steps of the described methods can be performed in a different order and still achieve desirable results. Other embodiments are within the scope of the following claims.

What is claimed is:

1. A computer-implemented method for examining a blood vessel wall comprising:
    illuminating, with a probe, the blood vessel wall with two or more wavelengths of near-infrared light;
    receiving, by the probe, reflected near-infrared light from the blood vessel wall;
    determining, by a computing device, a reflectance spectrum based on the reflected near-infrared light from the blood vessel wall;
    determining, by the computing device, whether the reflectance spectrum is indicative of a presence of a lipid core plaque (LCP) by applying an LCP classifier to the reflectance spectrum;
    determining, by the computing device, a thickness of an LCP cap by applying an LCP cap thickness classifier to the reflectance spectrum if the reflectance spectrum is indicative of the presence of the LCP; and
    displaying, on a display, indicia of the thickness of the LCP cap.

2. The method of claim 1, wherein the LCP cap thickness classifier comprises a mathematical model generated based on one or more sample reflectance spectra and associated histopathology data.

3. The method of claim 2, wherein the histopathology data comprises LCP cap thickness measurements.

4. The method of claim 1, wherein applying the LCP cap thickness classifier provides a probability that the thickness of the LCP cap exceeds a threshold thickness.

5. The method of claim 4, wherein the threshold thickness is approximately 0.4 millimeters.

6. The method of claim 4, wherein the threshold thickness is approximately 0.1 millimeters.

7. The method of claim 1, wherein applying the LCP cap thickness classifier provides a probability that the thickness of the LCP cap is less than a threshold thickness.

8. The method of claim 7, wherein the threshold thickness is approximately 0.4 millimeters.

9. The method of claim 7, wherein the threshold thickness is approximately 0.1 millimeters.

10. The method of claim 1, further comprising determining a thickness of the LCP cap by applying a second LCP cap thickness classifier to the reflectance spectrum if the reflectance spectrum is indicative of the presence of the LCP.

11. The method of claim 1, wherein the indicia of the thickness of the LCP cap comprises an indication that the thickness of the LCP cap exceeds a thickness threshold.

12. The method of claim 1, wherein the indicia of the thickness of the LCP cap comprises an indication that the thickness of the LCP cap is less than a thickness threshold.

13. A computer program product, tangibly embodied in a non-transitory computer readable storage medium, for examining a blood vessel wall, the computer program product including instructions being operable to cause a data processing apparatus to:
  receive a signal indicative of reflected near-infrared light from the blood vessel wall, the blood vessel wall having been illuminated with two or more wavelengths of near-infrared light;
  determine a reflectance spectrum based on the received signal;
  determine whether the reflectance spectrum is indicative of a presence of a lipid core plaque (LCP) by applying an LCP classifier to the reflectance spectrum;
  determine a thickness of an LCP cap by applying an LCP cap thickness classifier to the reflectance spectrum if the reflectance spectrum is indicative of the presence of the LCP; and
  display, on a display, indicia of the thickness of the LCP cap.

14. The computer program product of claim 13, wherein the LCP cap thickness classifier comprises a mathematical model generated based on one or more sample reflectance spectra and associated histopathology data.

15. The computer program product of claim 14, wherein the histopathology data comprises LCP cap thickness measurements.

16. The computer program product of claim 13, wherein applying the LCP cap thickness classifier provides a probability that the thickness of the LCP cap exceeds a threshold thickness.

17. The computer program product of claim 16, wherein the threshold thickness is approximately 0.4 millimeters.

18. The computer program product of claim 16, wherein the threshold thickness is approximately 0.1 millimeters.

19. The computer program product of claim 13, wherein applying the LCP cap thickness classifier provides a probability that the thickness of the LCP cap is less than a threshold thickness.

20. The computer program product of claim 19, wherein the threshold thickness is approximately 0.4 millimeters.

21. The computer program product of claim 19, wherein the threshold thickness is approximately 0.1 millimeters.

22. The computer program product of claim 13 including instructions being operable to cause the data processing apparatus to determine a thickness of the LCP cap by applying a second LCP cap thickness classifier to the reflectance spectrum if the reflectance spectrum is indicative of the presence of the LCP.

23. The computer program product of claim 13, wherein the indicia of the thickness of the LCP cap comprises an indication that the thickness of the LCP cap exceeds a thickness threshold.

24. The computer program product of claim 13, wherein the indicia of the thickness of the LCP cap comprises an indication that the thickness of the LCP cap is less than a thickness threshold.

25. A computer-implemented method for building a lipid core plaque (LCP) cap thickness classifier comprising:
  a. for each location of a plurality of locations on a plurality of blood vessel walls:
    illuminating, with a probe, the location with two or more wavelengths of near-infrared light;
    receiving, by the probe, reflected near-infrared light from the location;
    determining, by a computing device, a reflectance spectrum based on the reflected near-infrared light from the location;
    determining, by the computing device, whether the reflectance spectrum is indicative of a presence of an LCP at the location by applying an LCP classifier to the reflectance spectrum;
    selecting, by the computing device, the location if the reflectance spectrum is indicative of the presence of the LCP at the location; and
    receiving, by the computing device, histopathology data associated with the location;
  b. receiving, by the computing device, a cap thickness threshold; and
  c. generating, by the computing device, the LCP cap thickness classifier based on the reflectance spectrum and histopathology data of each selected location from step a. and the cap thickness threshold.

26. A computer program product, tangibly embodied in a non-transitory computer readable storage medium, for building a lipid core plaque (LCP) cap thickness classifier, the computer program product including instructions being operable to cause a data processing apparatus to:
  a. for each location of a plurality of locations on a plurality of blood vessel walls:
    receive a signal indicative of reflected near-infrared light from the location, the location having been illuminated with two or more wavelengths of near-infrared light;
    determine a reflectance spectrum based on the received signal;
    determine whether the reflectance spectrum is indicative of a presence of an LCP at the location by applying an LCP classifier to the reflectance spectrum;
    select the location if the reflectance spectrum is indicative of the presence of the LCP at the location; and
    receive histopathology data associated with the location;
  b. receive a cap thickness threshold; and
  c. generate the LCP cap thickness classifier based on the reflectance spectrum and histopathology data of each selected location from step a. and the cap thickness threshold.

27. A computer-implemented method for examining a blood vessel wall comprising:
  illuminating, with a probe, the blood vessel wall with two or more wavelengths of near-infrared light;
  receiving, by the probe, reflected near-infrared light from the blood vessel wall;
  determining, by a computing device, a reflectance spectrum based on the reflected near-infrared light from the blood vessel wall;
  determining, by the computing device, whether the reflectance spectrum is indicative of a presence of a lipid core plaque (LCP) by applying an LCP classifier to the reflectance spectrum;
  if the reflectance spectrum is indicative of the presence of the LCP:
    determining, by the computing device, a thickness of the LCP cap by applying a first LCP cap thickness classifier having a first threshold to the reflectance spectrum and applying a second LCP cap thickness classifier having a second threshold to the reflectance spectrum, wherein the first threshold is greater than the second threshold; and
  displaying, on a display, indicia of the thickness of the LCP cap.

* * * * *